United States Patent [19]

Okada

[11] Patent Number: 4,718,419
[45] Date of Patent: Jan. 12, 1988

[54] SNARE ASSEMBLY FOR ENDOSCOPE
[75] Inventor: Tsutomu Okada, Tokyo, Japan
[73] Assignee: Olympus Optical Co., Ltd., Japan
[21] Appl. No.: 890,629
[22] Filed: Jul. 30, 1986
[30] Foreign Application Priority Data Aug. 5, 1985 [JP] Japan .................... 60-172171
Sep. 17, 1985 [JP] Japan .................... 60-204820

[51] Int. Cl.⁴ .................................... A61B 17/36
[52] U.S. Cl. .................................... 128/303.15; 128/4
[58] Field of Search .................................... 128/4–8,
128/303.1, 303.13–303.17, 305, 751

[56] References Cited

U.S. PATENT DOCUMENTS

| | | | |
|---|---|---|---|
| 3,903,892 | 9/1975 | Komiya | 128/303.15 |
| 3,910,279 | 10/1975 | Okada et al. | 128/303.15 |
| 3,955,578 | 5/1976 | Chamness et al. | 128/303.15 |
| 4,103,680 | 8/1978 | Yoon | 128/303.15 |
| 404,181,131 | 1/1980 | Ogiu | 128/303.15 |
| 4,326,530 | 4/1982 | Fleury, Jr. | 128/303.14 |
| 4,485,812 | 12/1984 | Harada et al. | 128/303.15 |
| 4,618,885 | 10/1986 | Nagasaki et al. | 128/303.15 |

FOREIGN PATENT DOCUMENTS 55-126811 9/1980 Japan .

Primary Examiner—Max F. Hindenburg

[57] ABSTRACT

A snare assembly is disclosed which is inserted into a region of interest of a human body through a channel of an endoscope. The snare assembly comprises at least one flexible tube, a folded snare which is so inserted into the flexible tube as to be movable back and forth and having a folded end portion and a relatively short snare section, a slide means attached to a base end portion of the short snare section, and a stopper movable back and forth and, upon the forward movement of the slide means, abutting against the slide means to restrict an extension length of the short snare section. A fixing means is provided on the base end portion of the tube and stopper, whereby after a relative position between the tube and the stopper is adjusted the stopper and tube can be fixed at that relative position.

18 Claims, 23 Drawing Figures

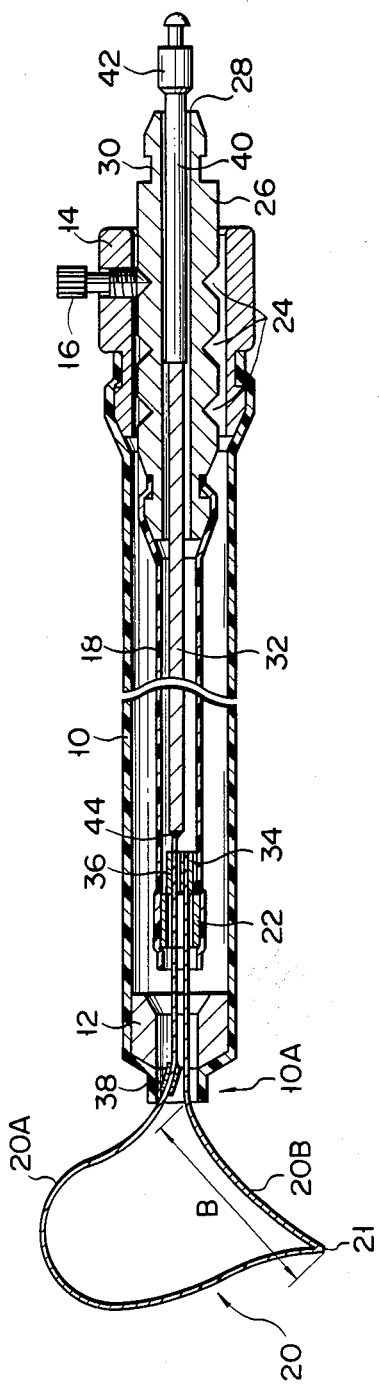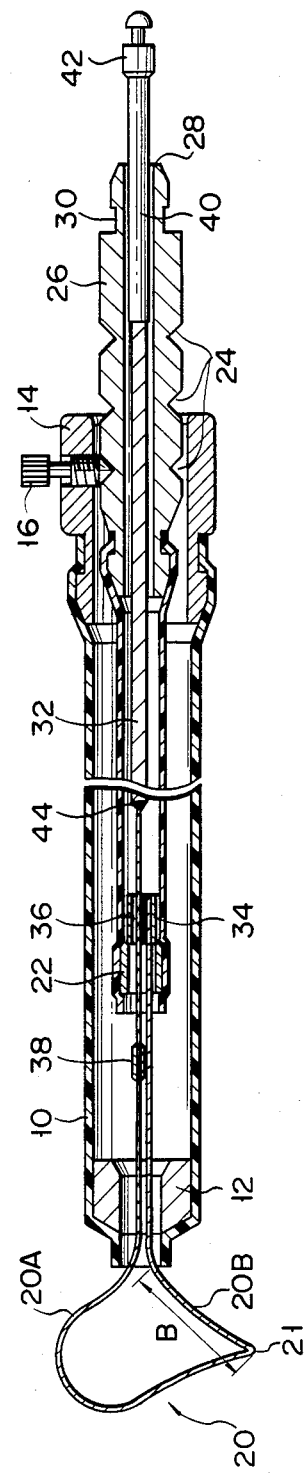

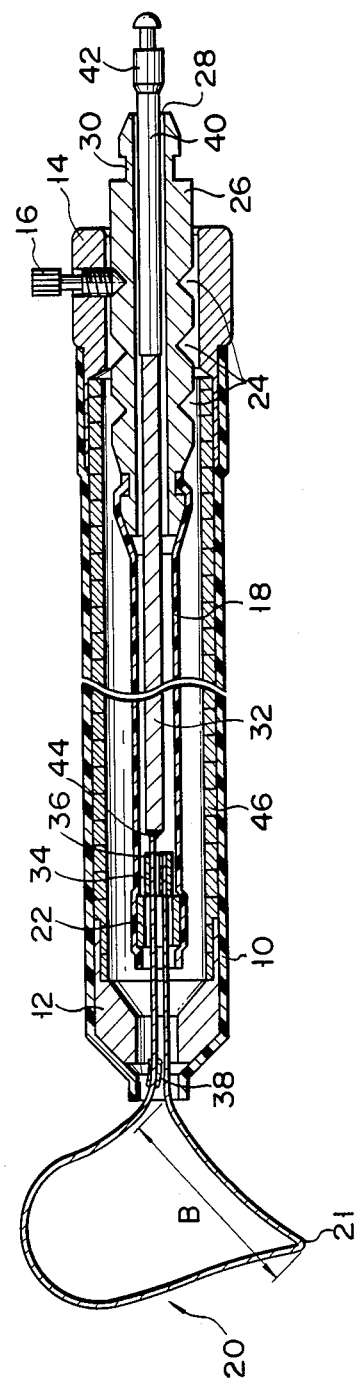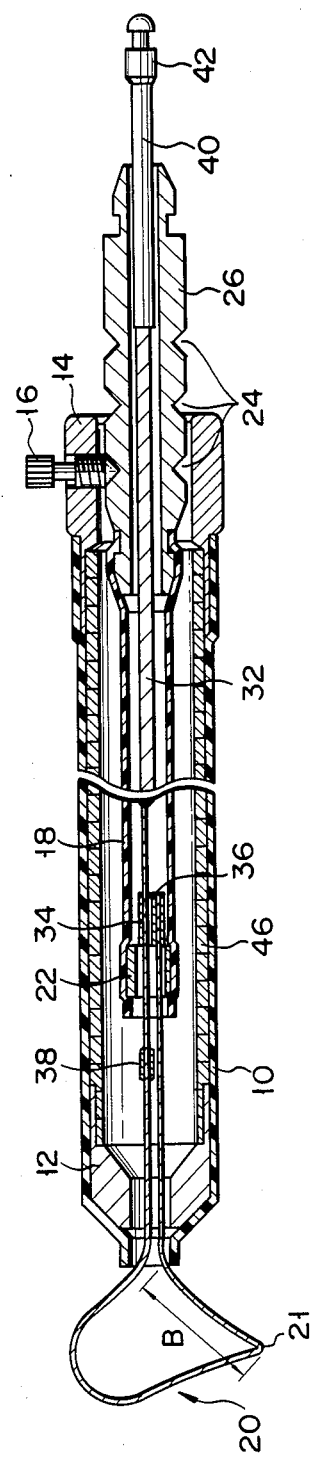

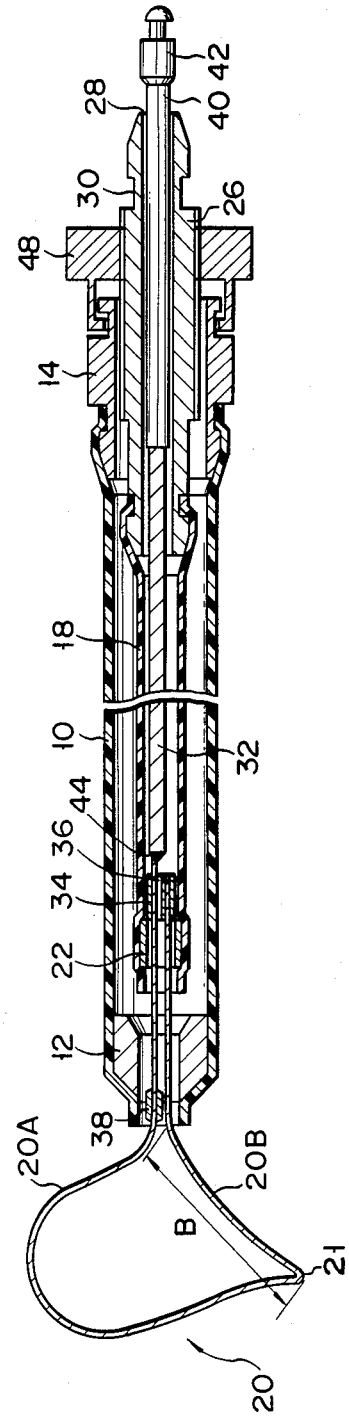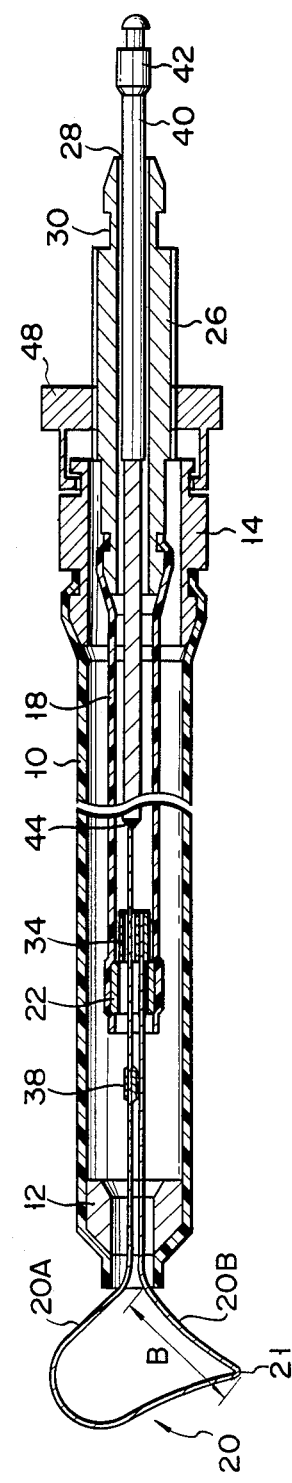

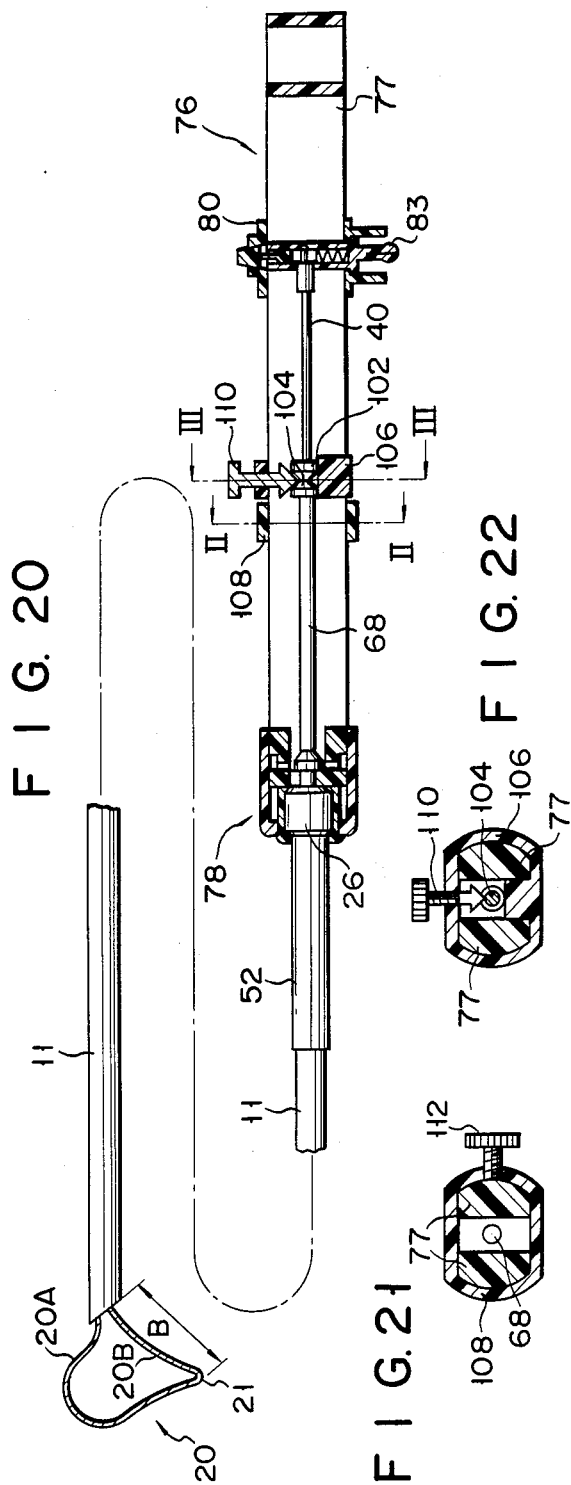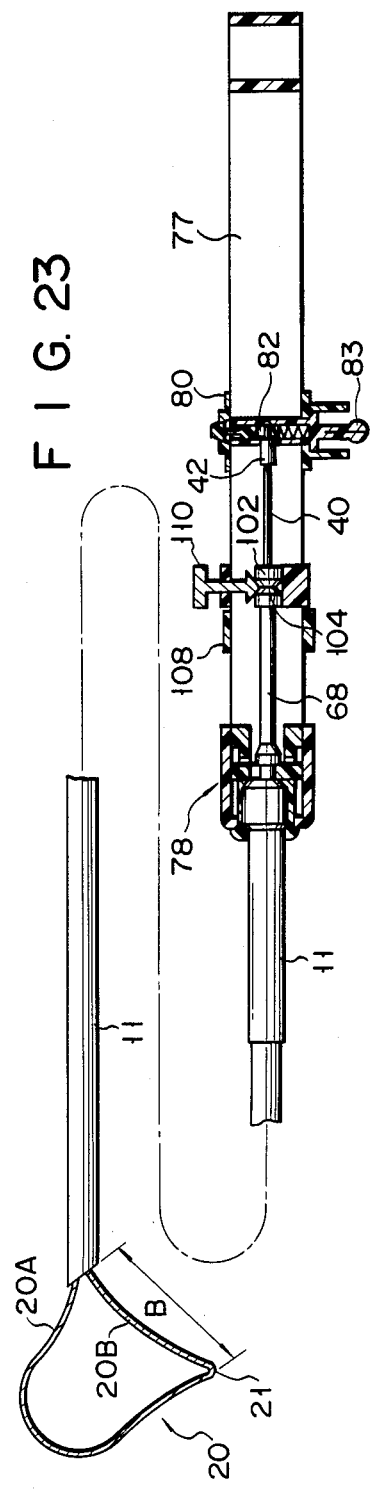

SNARE ASSEMBLY FOR ENDOSCOPE

BACKGROUND OF THE INVENTION

Field of the Invention

This invention relates to a snare assembly which is inserted into a region of interest of a human being through a channel of an associated endoscope, and in particular to a snare assembly which can cut, for example, a polyp in a body cavity of a human being by a current of a high frequency supplied to that location.

Description of the Prior Art

A conventional snare assembly for endoscope is disclosed in, for example, Japanese Utility Model Disclosure (KOKAI) No. 55-126811. In this snare assembly, a snare is inserted into a sheath such that a folded end portion is provided at the forward end portion of the snare with first a relatively long snare section and second a relatively short snare section defined by a folded point. A slide member is fixed to the end portion of the second snare section. The slide member has a small bore through which the end portion of the first snare section is inserted. A latching member is attached to the first snare section between the folded end portion and the slide member and, upon pulling the end of the first snare section, abuts against the slide member to move the slide member. In this connection it is to be noted that a stopper is mounted near the forward end of the sheath to stop the slide member from being dropped off the sheath.

In the snare assembly, when a polyp, for example, is to be cut, the end portion of the first snare section is pushed ahead, the slide member is advanced to a position of the stopper where it is stopped due to an abutment thereagainst. When the end portion of the first snare is more pushed ahead, the first snare section is curved to provide a semi-circular loop. With such a polyp entrapped within the loop, the end portion of the first snare section is withdrawn to permit the polyp to be tightened around the loop. A current of a high frequency is supplied to that location to cause the polyp to be rejected.

In the aforementioned conventional snare assembly, a constant extension length is provided between the forward end of the sheath and the folded end portion of the loop, failing to freely vary the size of such a semicircular loop. Therefore, there is a possibility of the snare loop failing to entrap an object, such as a polyp, having a greater or smaller size.

SUMMARY OF THE INVENTION

It is accordingly the object of this invention to provide a snare assembly for endoscope which can freely vary the size of a snare loop in accordance with the size of an object, such as a polyp.

In order to attain the aforementioned object a snare assembly for endoscope is provided which comprises:
a flexible outer tube having a forward end and base end;
a flexible inner tube inserted into the outer tube such that it can be moved back and forth, the inner tube having a forward end and base end;
a folded snare so inserted into the inner tube as to be movable back and forth and having folded end portion and a relatively short snare section;
a slide member attached to a base end portion of the short snare section and inserted into the inner tube such that it is movable there;
a stopper attached to the forward end of the inner tube to allow the slide member to abut thereagainst; and
fixing means mounted on the base ends of the inner and outer tubes and, after a relative position of the inner tube to the outer tube has been adjusted, fixing the inner tube to the outer tube at that relative position.

Another snare assembly is also disclosed which comprises:
a flexible tube;
a folded snare inserted into the tube to be movable back and forth and having a folded end portion and a relatively short snare section;
slide means attached to a base end portion of the short snare section;
stopper means movable back and forth and adapted to abut against the slide means upon the forward movement of the snare; and
fixing means guiding the slide means and stopper means in a moving direction and, after a relative position between the stopper means and the tube has been adjusted, fixing the stopper means and tube at that relative position.

BRIEF DESCRIPTION OF THE DRAWINGS

FIGS. 1 and 2 each are a cross-sectional view in side elevation showing a snare assembly for endoscope according to one embodiment of this invention;

FIGS. 3 and 4 each are a cross-sectional view in side elevation showing a variant of an outer tube of the snare assembly of this invention;

FIGS. 5 and 6 each are a cross-sectional view in side elevation showing another variant of a fixing means of the snare assembly of this invention;

FIGS. 20 and 23 each are a cross-sectional view schematically showing a variant of the operation device attached to the sheath assembly of the snare assembly of this invention;

FIG. 21 is a cross-sectional view showing the operation device, as taken along II—II line in FIG. 20; and FIG. 22 is a cross-sectional view, as taken along III—III line in FIG. 20.

DETAILED DESCRIPTION OF THE PREFERRED EMBODIMENTS

Figure 7:
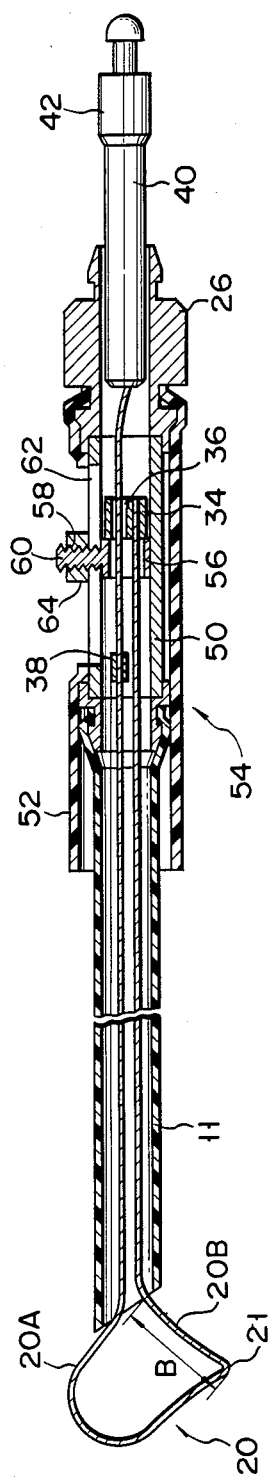
FIGS. 7 and 8 each are a cross-sectional view in side elevation showing the snare assembly according to another embodiment of this invention.

The embodiments of this invention will be explained below with reference to the accompanying drawings.

FIGS. 1 and 2 shown a snare assembly for endoscope according to a first embodiment of this invention. In the first embodiment, outer tube 10 is formed of a flexible resin having an electrical insulation property, such as Teflon, and has narrow section 10A at the forward end. Cylindrical rigid tip 12, such as a metal, is fitted inside outer tube 10 and has the same inner diameter as that of narrow section 10A. Cylindrical cap 14 made of, for example, a metal is attached to the base end portion of outer tube 10 and set screw 16 is screwed to cylindrical cap 14.

Inner tube 18 is formed of a flexible resin having an electrical insulation property, such as Teflon, and inserted into outer tube 10 such that snare 20 is inserted into inner tube 10. Cylindrical stopper 22 is fitted inside the forward end portion of inner tube 18. Cap 26 is attached to the base portion of inner tube 18 and has grooves 24 formed at predetermined pitches on its outer surface. Insertion hole 28 is formed in cap 26 in a longitudinal direction and fixing section 30 is formed at the base portion of cap 26 to fix an operation device, not shown, there.

The forward end portion of snare 20 is folded at a proper place to provide folded point 21 with a first, relatively long snare section 20A and second, relatively short snare section 20B defined thereby. Slide member 34 is fixed to the end of second snare section 20B of snare 20. Slide member 34 is movably disposed within inner tube 18 such that first snare section 20A is movably inserted into hole 36 of slide member 34. Engaging member 38 is fixed, ahead of hole 36 of slide member 34, to first snare section 20A to move slide member 34 upon withdrawing the end of first snare section 20A. Base end portion of first snare section 20A extends toward the base portion of inner tube 18 through the hole 36 of slide member 34, and thick operation wire 32 is connected to the base end portion of first snare section 20A. As snare 20 use may be made of a center wire, such as operation wire 32. The other wires around center wire 20 are deposited, at the forward end, with solder 44. Operation rod 40 is connected at one end to the base end of operation wire 32 and at the other end portion to an operation device, not shown, by means of fixing member 42.

The operation of the first embodiment will be explained below.

Snare 20 is freely moved back and forth by pulling and pushing operation rod 40. When snare 20 is pushed forward, slide member 34 is advanced into abutment with stopper 22 with the result that further advance of folded point 21 of snare 20 is stopped. At this time, folded point 21 of snare 20 is located at the most forward position. Further advance of operation rod 40 causes first snare section 20A to be outwardly curved from folded point 21 to provide a substantially elliptical loop, as shown in FIG. 1, in which case the length B of first snare section 20B extending from the forward end of outer tube 10 to folded point 21 is constant. First snare section 20A is moved back and forth by pulling and pushing operation rod 40 so that the aforementioned loop is closed and opened. In order to vary the size of the snare loop it is necessary to vary the extension length B of second snare section 20B. To this end, cap 26 is pulled as shown, for example, in FIG. 2 and thus inner tube 18 is retracted relative to outer tube 10 in a direction of the base end of outer tube 10, so that stopper 22 at the forward end portion of inner tube 18 is moved away from the forward open end of outer tube 10. Since, therefore, the whole length of second snare section 20B is constant, the extension length B of second snare section 20B is shortened to an extent to which inner tube 18 has been retracted.

By turning the forward end of set screw 16 into one of grooves 24 of cap 26, inner tube 18 is fixed there.

With the snare assembly of this invention, it is possible to vary the extension length B of second snare section 20A in accordance with the size of an object within a human body, such as a polyp. With the snare loop set to an optimum size a current of a high frequency is supplied to the snare loop, whereby the polyp within the living body can be rejected.

FIGS. 3 and 4 show a variant of an outer tube of a snare assembly according to this invention. In the variant, densely-turned coil 46 is provided on the inner surface of the outer tube made of a synthetic resin.

When operation rod 40 is pulled back with a polyp firmly entrapped by a loop of snare 20, a longitudinal compressive force acts upon the outer tube. However, that compressive force is positively received on coil 46. As a result, a pull which is effected by operation rod 40 is transmitted to snare 20 where the polyp is strongly clamped so that it can positively and readily been rejected by a current of a high frequency.

FIGS. 5 and 6 show a variant of a fixing means of this invention which fixes an inner tube to an outer tube. In this variant, adjusting screw 48 is threadably mounted in inlet member 14 which in turn is fixed to outer tube 10. An internally threaded portion on the inner surface of adjusting screw 48 is inserted over an externally threaded portion on the outer surface of inner tube 18.

By turning adjusting screw 48, inner tube 18 is moved back and forth relative to, and within, outer tube 10 and to a certain position where it is fixed there.

In this variant, the extension length B of a snare loop is arbitrarily set so that a proper loop of an optimum size can be provided there.

Figure 8:
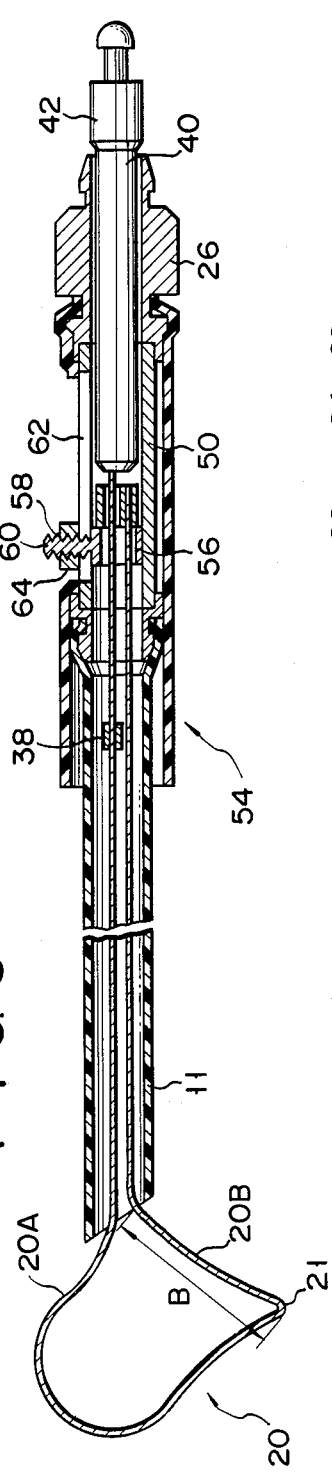
Figure 9:
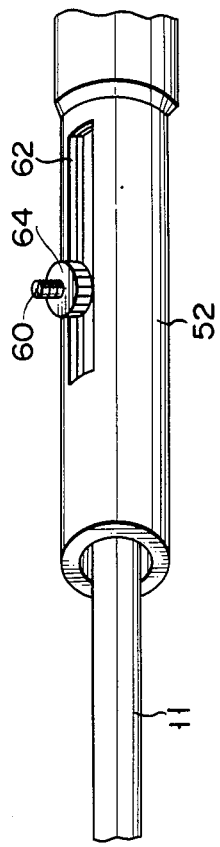
FIG. 9 is a perspective view showing a sheath assembly for the snare assembly of this invention.

FIGS. 7 to 9 show a snare assembly according to a second embodiment of this invention in which case an tube (11) corresponding to the outer tube 10 in the first embodiment is formed of a flexible resin having an electrically insulating property, such as Teflon. Annular stopper holder 50 is coupled to the base end portion of tube 11. Sheath 52 covers the base end portion of tube 11 and outer surface of stopper holder 50 to protect these members. Cap 26 is mounted to the base end portion of stopper holder 50. These associated members constitute sheath assembly 54.

Adjusting stopper 56 is slidably inserted within stopper holder 50 and equipped, at an outer periphery, with projection 60 having threaded section 58. Projection 60 extends outwardly through an elongated hole (62) formed longitudinally of stopper holder 50 and sheath 52. Nut 64 is threaded over the forward end portion of projection 60 and, upon being tightened up, can fix adjusting stopper 56 at a proper place within a range of elongated hole 62 of stopper holder 50.

Snare 20 is inserted into sheath assembly 54 such that it can be pulled or pushed there. Slider 34, engaging member 38, operation rod 40 and fixing member 42 are the same as those in the first embodiment. In this second embodiment, the base end of snare 20 is connected directly to operation rod 40 and the aforementioned operation wire (32) is not provided in this embodiment.

The operation of the second embodiment will now be explained below.

First, adjusting stopper 56 is moved to a proper position by loosening nut 64. At this time, projection 64 can be moved along elongated hole 62 and adjusting stopper 56 can be moved without being turned within stopper holder 50. The fixing position of adjusting stopper 56 is selected as follows. That is, as shown in FIG. 7, operation rod 40 is advanced, causing snare 20 to be pushed forward so that a snare portion in the neighborhood of folded portion 21 extends from the forward end of tube 11 to provide a snare loop. Slide member 34 abuts against adjusting stopper 56 and, in this state, the extension length B of first snare section 20B is set to a proper extent where nut 64 is tightened up to cause stopper 56 to be fixed.

In order to give a greater extension length B to the snare loop, it is only necessary that, as shown in FIG. 8, adjusting stopper 56 be so selected as to cause adjusting stopper 56 to be located to a more advanced position. In this way, adjusting stopper 56 is fixed to a properly selected position so that the size of the snare loop can be freely adjusted.

Figure 10:
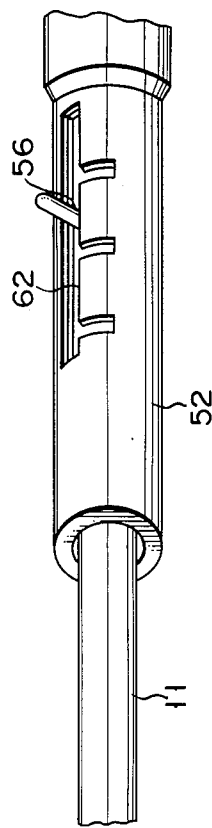
FIGS. 10 and 11 each are a perspective view showing a variant of the sheath assembly for the snare assembly of this invention.
Figure 11:
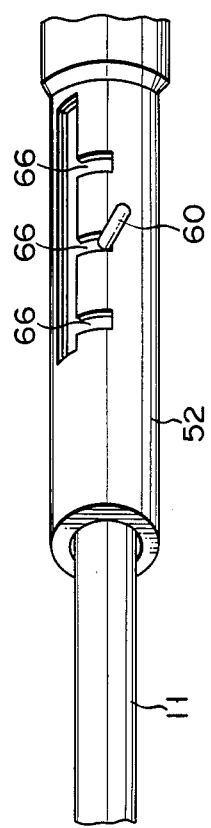
Figure 12:
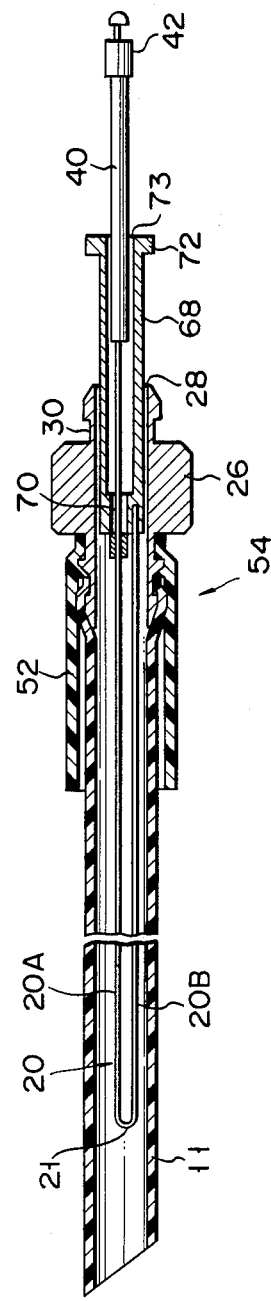
FIG. 12 is a cross-sectional view in side elevation showing a second variant of the sheath assembly of the snare assembly of this invention.

FIGS. 10 and 11 shown a variant of the sheath assembly according to the snare assembly of FIGS. 7 to 9. In this variant, a different fixing means is used for adjusting stopper 56. That is, a plurality of recesses 66 are formed in elongated hole 62 in a direction of an outer periphery of stopper holder 50 and sheath 52. Respective recesses 66 are formed at proper intervals and, upon being engaged by projection 60 of adjusting stopper 56, are fixed to that position.

FIGS. 12 to 19 show another variant of the sheath assembly. In sheath assembly 54 of this variant, cap 26 is mounted on the base end portion of tube 11, and that mounting portion and base end portion of tube 11 are surrounded by sheath 52. Slide pipe 68 having small hole 70 at the forward end and latching section 72 at the base end portion is inserted into insertion hole 28 of cap 26. Operation rod 40 is inserted into slide pipe 68 through an opening (73). Snare 20 inserted into tube 11 has folded portion 21 and disposed such that the end of second snare section 20B is connected to the forward end portion of slide pipe 68 and the end of first snare section 20A extends into slide pipe 68 through the small hole (70) and is connected to the forward end of operation rod 40.

Figure 13:
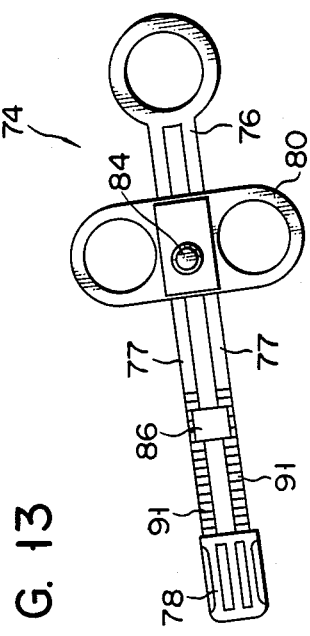
FIG. 13 is a plain view showing an operation device associated with the second variant of the sheath assembly of FIG. 12.

FIG. 13 shows operation device 74 which is attached to sheath assembly 54. The operation device has body 76 comprises of a pair of guide rails 77, 77. Member 78 on which cap 26 of the sheath assembly is fixed is provided on the forward end portion of body 76 of operation device 74. Slide member 80 for operation is so provided that it is movable back and fourth along guide rails 77, 77. As seen from FIG. 14, plug 83 and engaging member 82 for attaching fixing section 42 of operation rod 40 to slide member 80 are mounted on slide member 80. Push button 84 is attached to the upper area of engaging member 82 and spring 85 is located beneath engaging member 82. The engaging and disengaging of fixing section 42 of operation rod 40 with and from engaging member 82 is achieved by the operation of the push button.

Adjusting stopper 86 for adjusting the fixing position of slide pipe 68 is located between attaching member 78 and slide member 80 and between guide rails 77 and 77.

Figure 14:
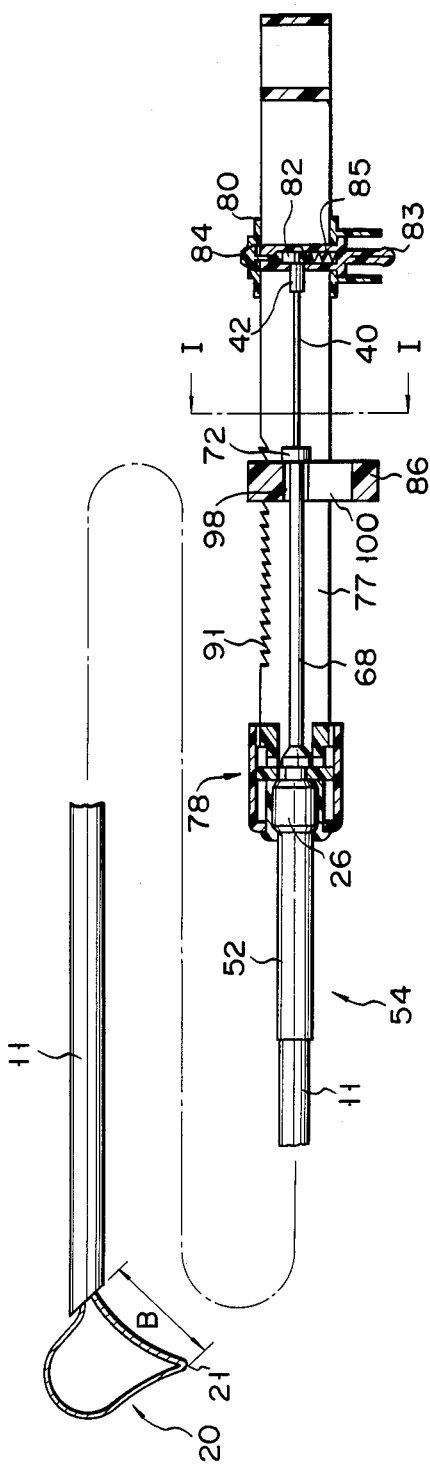
FIGS. 14 and 19 are a cross-sectional views in side elevation schematically showing the sheath assembly and associated operation device.
Figure 18:
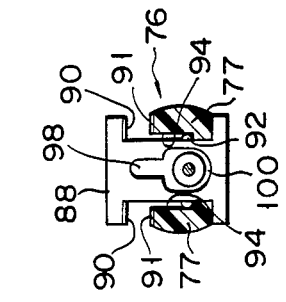
FIGS. 15 and 18 each are a cross-sectional view, as taken along I—I line in FIG. 14, showing the operation device of FIG. 14.
Figures 16, 17:
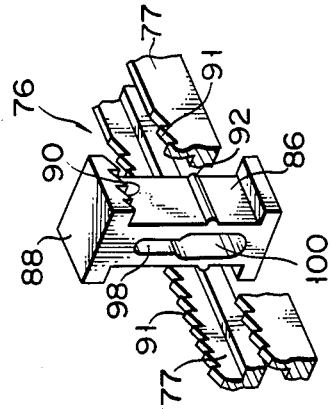
FIGS. 16 and 17 are a perspective views schematically showing a guide rail and stopper for the operation device of the snare assembly of this invention.
Figure 15:
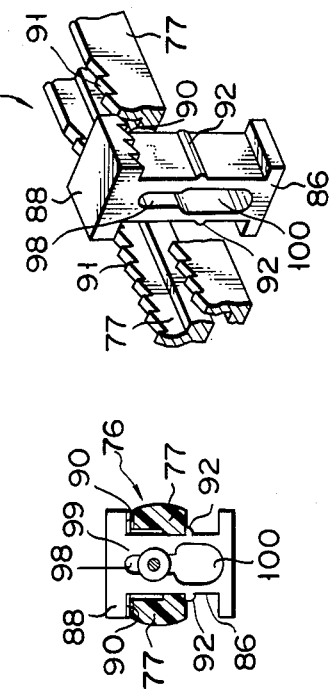

As seen from FIGS. 15 to 18, adjusting stopper 86 is formed of a block member of an I configuration with serrations 90 formed at the lower surfaces of opposite side flanges of the top of the block member. Respective serrations 90 engage with corresponding serrations 91 which are formed on the top surfaces of the forward portions of respective guide rails 77 and 77. FIGS. 14 to 16 show the state in which adjusting stopper 86 engages with the guide rails. Adjusting stopper 86 is so provided that it can be moved up and down relative to guide rails 77 and 77. As shown in FIGS. 17 and 18, adjusting stopper 86 upon being moved to an upper position allows its serrations 90 to disengage from serrations 91 of operation device 74 so that adjusting stopper 86 can slide in the forward and backward directions. Click 92 is formed on the side surface of the body of adjusting stopper 86. As shown in FIG. 15, click 92 engages with the lower surface of guide rail 77 upon lowering adjusting stopper 86 and, as shown in FIG. 18, engages with click groove 94 on the inner wall of guide rail 77 upon raising adjusting stopper 86, whereby these upper and lower positions are maintained.

Upper small bore 98 and lower large bore 100 are formed as a single keyhole at the sides of the body of adjusting stopper 86 to permit small bore 98 to communicate with large bore 100. Large bore 100 permits insertion of operation rod 40 and slide pipe 68. When adjusting stopper 86 is lowered, the rear end edge (99) of small hole 98 engages with engaging member 72 of slide pipe 68. When adjusting stopper 86 is raised, large hole 100 permits insertion of engaging member 72 of slide pipe 68.

After the assembly of sheath assembly 54 and operation device 74 as shown in FIG. 14, the snare assembly is clinically applied. The sheath assembly and operation device are assembled as follows.

At first, as shown in FIGS. 17 and 18, adjusting stopper 86 is raised such that large bore 100 is located at the middle of guide rails 77 and 77. Then, cap 26 of sheath assembly 54 is attached to member 78 and engaging member 72 of slide pipe 68 is inserted through the large hole (100). Then adjusting stopper 86 is pushed down to permit the body of slide pipe 68 to be located within the small hole 98. At this time, slide pipe 68 abuts against rear end edge 99 of small bore 98, thereby preventing slide pipe 68 from being moved forward beyond that position. Fixing portion 42 of operation rod 40 is fixed to engaging member 82 of slide member 80.

Figure 19:
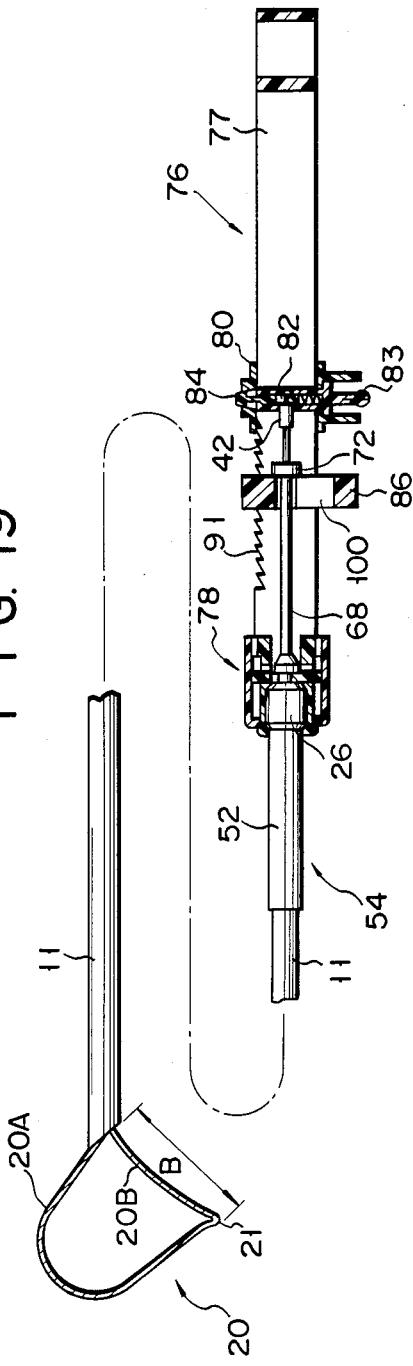

In the clinical application of the snare assembly as set forth above, slide member 80 is pushed forward to allow the snare to be advanced. At the same time, slide pipe 68 is also moved forward, and snare 20 is projected from the forward end of sheath 11. When, however, engaging member 72 of slide pipe 68 abuts against adjusting stopper 86, then slide pipe 80 stops its forward movement. Upon the further pushing of the slide member 80, snare 20 projected from the forward end of sheath 11 is provided a loop. The snare loop is comprised of folded area 21 and first and second snare sections 20A and 20B, and an extension length B of second snare portion 20B corresponds to the position of adjusting stopper 86. FIG. 19 shows the state in which slide member 80 is pushed forward. As will be appreciated from FIG. 19, the extension length B becomes greater upon the forward movement of adjusting stopper 86 and becomes smaller upon the backward movement of adjusting stopper 86. The position of adjusting stopper 86 can be set by pushing adjusting stopper 86 out of engagement with serrations 90 and 91, slidably moving the stopper forward and bockward and lowering the stopper to cause serration 90 to engage with serration 91.

FIGS. 20 to 23 show a variant of an operation device. A sheath assembly of the variant has slide pipe 68 as in the case of the aforementioned second variant. Fixing body 102 is mounted on the base end of slide pipe 68 and has V-groove 104 on the outer periphery. As shown in FIGS. 20 and 23, slide member 106 of a collapsed ring configuration has tighting screw 110 engageable with V-groove 10 of fixing body 102 and is attached around the pair of guide rails 77, 77 of operation body 76. As shown in FIGS. 20 and 21, stopper 108 of a collapsed ring configuration is provided ahead of slide member 106 and around the pair of guide rails 77, 77 and has fixing screw 112. If the forward end of tightening screw 110 of slide member 106 engages with V-groove 104 of fixing body 102, slide member 106 and fixing body 102 are both moved as one unit. Stopper 108 can be freely moved along the guide rails after fixing screw 112 has been loosened. By fixing the stopper (108) with fixing screw 112 to a proper position, slide member 106 is set to that position, with the result that slide pipe 68 is set to a corresponding stop position to determine an extension length B of the snare loop corresponding to that stop position. The extension length B can be adjusted by shifting the fixing position of stopper 108.

Since in the snare assembly the size of the snare loop can freely be set, it is possible to readily select the size of a loop enough great to allow entrapment of an object within a living body, such as a polyp. With that polyp entrapped with the snare loop, a current of a high frequency is supplied to the snare, permitting the polyp to be cut readily and positively.

What is claimed is:

1. A snare assembly for an endoscope comprising a flexible outer tube having a forward end and a base end; a folded snare inserted into said tube to be movable back and forth and having a folded end portion and a relatively short snare section extending from a base end portion of the snare to the folded end portion;
    slide means attached to the base end portion of the short snare section and having the snare section extending therein;
    stopper means slidably positioned within said flexible tube to be movable back and forth within said flexible tube to change the longitudinal position of said stopper means relative to said flexible tube, said stopper means abutting against said slide means upon the forward movement of said snare beyond a predetermined position; and
    first releasable fixing means on said stopper means and second releasable fixing means on said flexible tube, said first fixing means being movable with said stopper means and being releasably attachable to said second fixing means for releasably fixing the stopper means to said tube at a selected relative position for changing the distance said relatively short snare section extends from the forward end of said flexible tube.

2. A snare assembly according to claim 1, wherein said stopper means comprises:
    a flexible innner tube inserted into said flexible outer tube such that it can be moved back and forth, the inner tube having a forward end and a base end; and
    a stopper attached to the forward end of the inner tube to allow said slide means to abut thereagainst.

3. A snare assembly according to claim 2, in which said first fixing means comprises:
    a cap mounted on the base end portion of the inner tube, having a plurality of grooves formed on the outer surface of the cap, and permitting said snare to be inserted therein; and
    an inlet member mounted on the base end portion of said outer tube, having a fixing screw for abutting against the groove of the cap inserted into the member.

4. A snare assembly according to claim 2, in which said first fixing means comprises:
    a cap mounted on the base end portion of said inner tube, having an externally threaded portion on its outer surface portion and allowing insertion of said snare;
    an inlet member mounted on the base end portion of said outer tube, having a groove on its outer surface, and allowing insertion of said cap; and
    an adjusting screw having an internally threaded portion engaging with said externally threaded portion and annular projection engaging with the groove of the inlet member.

5. A snare assembly according to claim 2, further comprising a densely turned coil provided on the inner surface of said outer tube.

6. A snare assembly according to claim 3, further comprising operation means connected to the base end portion of said snare and inserted into said cap to be movable back and forth.

7. A snare assembly according to claim 4, further comprising operation means connected to the base end portion of said snare and inserted into said cap to be movable back and forth.

8. A snare assembly according to claim 1, wherein said second fixing means guides said slide means and stopper means.

9. A snare assembly according to claim 8, in which said stopper means and said second fixing means are incorporated into an operation device which is separable from said snare, said tube, said slide means and a cap connected to the base end portion of said tube.

10. A snare assembly according to claim 9, in which said slide means is comprised of a slide pipe so inserted into the base portion of said tube as to be movable back and forth and having an annular projection at a base end portion and, said annular projection engaging with said stopper means of said operation device.

11. A snare assembly according to claim 10, in which said operation device comprises:
    an operation selection body having a pair of guide rails each having a serration on the upper surface;
    an adjusting stopper of an I-shaped block member having a head section having a serration at each undersurface of opposite flanges which corresponds to the serration of the guide rail, a large hole formed at a lower portion of a middle portion of the I-shaped block member to allow said annular projection of said slide pipe to pass therethrough and small hole formed at an upper portion of the middle portion to communicate with said large hole, said small hole allowing a body of said slide pipe to pass therethrough, and said adjusting stopper being so provided as to allow an up-and-down movement between the guide rails;

a slide member for operation which is so provided at the rear portions of said guide rails as to be movable back and forth and to which the base end portion of said snare is connected; and attaching means for coupling said operation section body to a cap for said tube.

12. A snare assembly according to claim 11, in which said adjusting stopper has a pair of clicks each substantially at the middle portion of said body and said guide rails have a pair of click grooves which allow said clicks to engage at their inner surfaces.

13. A snare assembly according to claim 10, in which said operation device comprises:

an operation section body having a pair of guide rails;

a collapsed-ring-like slide member mounted around said pair of guide rails and having a tightening screw for engaging with a V-groove formed on the engaging portion of said slide pipe;

a collapsed-ring-like stopper mounted around the pair of guide rails, located ahead of said slide member and having a fixing screw;

a slide member for operation which is so mounted at the rear side of said guide rails as to be movable back and forth and which is connected to the base portion end of said snare; and attaching means for coupling said operation section body to a cap for said tube.

14. A snare assembly according to claim 8, in which said second fixing means has a stopper holder connected to the base end of said tube for receiving said slide means to permit such slide means to slide and having an elongated hole defined in said stopper holder in a longitudinal direction; and said stopper means having a stopper disposed therein closer to the forward end of said flexible inner tube than said slide means, said stopper having a projection extending through the elongated hole and allowing the stopper to move between ends of the elongated hole, and latching means for latching said projection to said stopper holder adjacent to said elongated hole.

15. A snare assembly according to claim 14 wherein said latching means includes a thread means on said projection and a threaded nut adapted to be threadably mounted on said projection.

16. A snare assembly for an endoscope comprising:

a flexible tube having a forward end and a base end;

a folded snare inserted into the tube to be movable back and forth and having a folded end portion and a snare section which is short relative to said folded end portion;

slide means attached to a base end portion of the short snare section;

stopper means movable back and forth and adapted to abut against said slide means upon the forward movement of said snare, said stopper means comprising a stopper disposed adjacent to said slide means and having a projection extending out from an elongated hole defined in said stopper means; and fixing means for fixing the stopper means and tube at a relative position between the stopper means and tube, after that relative position has been adjusted, said fixing means being adapted to guide said slide means and said stopper means, said fixing means further including a stopper holder connected to the base end of said tube, receiving said slide means to permit it to slide and having said elongated hole in a longitudinal direction and latching means for latching said projection to said stopper holder.

17. A snare assembly according to claim 16, in which said projection of said stopper is comprised of an externally threaded portion and said latching means comprises a nut which is threadably inserted over said outwardly threaded portion.

18. A snare assembly according to claim 16, in which said latching means is comprised of a plurality of engaging holes formed in a direction of the periphery of said elongated hole of said stopper holder and said projection of said stopper.

* * * * *